United States Patent [19]

Masiero et al.

[11] Patent Number: 5,475,168
[45] Date of Patent: Dec. 12, 1995

[54] PROCESS FOR PURIFYING 1,1,1-TRIFLUORO-2-FLUOROETHANE

[75] Inventors: Antonio Masiero, Padua; Paolo Cuzzato, Treviso; Letanzio Bragante, Padua, all of Italy

[73] Assignee: Ausimont S.p.A., Milan, Italy

[21] Appl. No.: 243,066

[22] Filed: May 16, 1994

Related U.S. Application Data

[63] Continuation of Ser. No. 995,127, Dec. 22, 1992, abandoned.

[30]    Foreign Application Priority Data

Dec. 23, 1991 [IT] Italy .................................. MI91A3465

[51] Int. Cl.$^6$ ..................................................... C07C 17/38
[52] U.S. Cl. ............................................................. 570/177
[58] Field of Search ..................................... 570/166, 169, 570/177

[56]    References Cited

U.S. PATENT DOCUMENTS

| | | |
|---|---|---|
| 3,235,612 | 2/1966 | Asello . |
| 3,755,477 | 8/1973 | Firth . |
| 3,992,325 | 11/1976 | Knaak ..................................... 570/169 |
| 4,129,603 | 12/1978 | Bell . |
| 4,158,675 | 6/1979 | Potter ..................................... 570/166 |
| 4,948,479 | 8/1990 | Brooks et al. . |
| 5,001,287 | 3/1991 | Fernandez et al. . |

*Primary Examiner*—Alan Siegel
*Attorney, Agent, or Firm*—Bryan Cave

[57]    ABSTRACT

1,1,1-trifluoro-2-fluoroethane (CFC 134a) is purified from 1,1-difluoro-2-chloroethylene (CFC 1122) by reacting a mixture comprising said compounds with hydrofluoric acid, at temperatures from 200° C. to 450° C., in the presence of chrome oxide ($Cr_2O_3$) in substantially crystalline form.

3 Claims, No Drawings

PROCESS FOR PURIFYING 1,1,1-TRIFLUORO-2-FLUOROETHANE

This is a continuation, of U.S. application Ser. No. 07/995,127, filed Dec. 22, 1992 now abandoned.

The present invention relates to a process for purifying, 1,1,1- trifluoro-2-floroethane (hereinafter referred to as 134a) from impurities consisting of 1,1-difluoro-2-chloro-ethylene (hereinafter referred to as 1122).

It is known how to prepare 134a by fluorination of $CF_3CH_2Cl$ (hereinafter referred to as 133a). Such a preparation method always leads also to the obtainment of 1122, the toxicity of which is known.

Therefore the need is felt to have available 134a as free as possible from 1122.

The separation of 1122 from 134a by means of physical methods, for example fractionated distillation, is extremely difficult.

It has been suggested to convert the 1122 contained in the 134a into more easily separable compounds by means of oxidation with hydrogen peroxide, or with permanganates (U.S. Pat. No. 4,129,603). Such a solution, however, is not very practical as it involves several onerous treatments in moist conditions, with production of great volumes of effluents difficult to be disposed off, particularly when great volumes of 134a to be purified must be treated.

Other suggested methods, such as chlorination with elemental chlorine in the presence of U.V. radiations (U.S. Pat. No. 4,948,479) and catalytic hydrogenation (U.S. Pat. No. 5,001,287) are not applicable on an industrial scale.

According to U.S. Pat. No. 4,158,675 it is possible to separate 1122 from 134a, up to residual concentrations of 1122 lower than 10 p.p.m., by reacting 1122 with HF in the presence of a catalyst consisting of $Cr_2O_3$, so as to convert it to $CF_3CH_2Cl$, which, having a boiling temperature higher by 30° C. than the one of 134a, can be subsequently distilled-off from the latter.

In this case, however, the Applicant has observed that during the reactivation of the catalyst with air, considerable amounts of volatile and very toxic hexavalent chrome oxyfluoride ($CrO_2F_2$) form and are then dispersed in the environment. Furthermore, another drawback of such process resides in the necessity that the reagent mixture should be prevailingly composed by HF; such a fact—considering that the mixture coming from the 134a production reaction and containing little more than 3% of 134a must be fed to the purification reactor—strongly limits the capability of the process of meeting great production requirements.

Thus, there was the need to have available a catalyst and a process not affected with said drawbacks.

An object of the present invention is to provide a process for purifying 134a from 1122, which is free from the abovesaid drawbacks and comprises reacting, in the gas phase, 1122 in admixture with 134a, with HF in the presence of substantially crystalline chrome oxide ($Cr_2O_3$) as a catalyst, at temperatures ranging from 200° to 450° C., but preferably from 250° to 380° C. and even more preferably from 250° to 360° C.

By "substantially crystalline chrome oxide" is meant herein a chrome oxide ($Cr_2O_3$) in which the crystalline form is present for at least 60%.

With respect to the process described in U.S. Pat. No. 4,158,675, which utilizes chrome oxide prepared by methods which provide an amorphous or substantially amorphous chrome oxide, the process of the present invention advantageously permits to operate with HF amounts slightly exceeding the stoichiometric amounts, with respect to 1122, wherefore for the treatment of 134a containing 1–2% of 1122 (representative value of the real industrial process) it is sufficient to feed the purification reactor with a mixture having a HF content of about 10%.

This permits, the contact times being equal, to use a much smaller and much more economic reactor than the one required by the process of the above-cited U.S. patent.

Furthermore, the crystalline chrome oxide, as compared with the amorphous chrome oxide, does not cause, during the indispensable regeneration with air, the formation of hexavalent chrome and therefore the formation of toxic and volatile oxyfluorides $CrO_2F_2$.

The crystalline chrome oxide to be used as a catalyst in the process of the invention can be utilized as such or it can be carried on at least partially fluorinated alumina. In the latter case the catalyst is particularly useful to carry out the process on a fluidized bed. An alumina fluorinated for at least 90% by weight is preferred as a carrier.

The catalyst utilized in the process according to the invention, when it is in the non-carried form, is prepared by calcining, preferably but not necessarily in air, the chrome hydroxide in the dried state, at temperatures higher than 420° C. up to temperatures of about 900° C., and preferably ranging from 500° to 850° C. and even more preferably from 550 to 700° C.

Calcination can be conducted in air or in an inert medium. The first case is preferred as it permits to operate at lower temperatures than in the second case.

When the catalyst is in the carried form, it can be prepared by impregnating the carrier, consisting of at least partially fluorinated alumina, with an aqueous solution of $CrCl_3 \cdot 3H_2O$, preferably operating in successive stages and drying time by time. The catalyst is then charged into a tubular reactor and fluidized during a few hours with an air flow at temperatures higher than 350° C. and preferably ranging from 400° to 500° C., at which temperatures, in the specific case in which it is in the carried form, the chrome compound is converted at least prevailingly to $Cr_2O_3$ in crystalline form. It is possible to employ higher temperatures than the ones cited above, but they do not offer further particular advantages.

The starting chrome hydroxide is preparable according to known methods, for example by precipitation from aqueous solutions of a chrome salt such as chloride, sulphate, etc., by means of sodium hydroxide or ammonium hydrate, followed by drying at temperatures up to 300° C., grinding, extrusion and final drying.

In case of exhaustion, the chrome oxide catalyst of the invention can be reactivated by treatment in air at about 400° C. for 4 hours.

The process of the invention can be carried into effect by causing the reaction mixture, comprising HF, 134a, 1122 (and optionally other products which have been utilized or have formed during the preparation of 134a by fluorination of trichloroethylene and/or of 133a) to flow through a tubular reactor maintained at the reaction temperature, filled with crystalline $Cr_2O_3$ in pellets, or with carried $Cr_2O_3$, as mentioned hereinbefore.

The following examples are given to illustrate the invention, but not to limit the scope thereof.

EXAMPLE 1

Preparation of the catalyst

A water solution of potassic chrome alum was treated with $NH_4OH$, thereby obtaining the precipitation of chrome hydroxide in the form of gel. This was washed with water, dried in air at a temperature of about 300° C., ground, kneaded with water, the resulting paste being then extruded in the form of small cylinders having a diameter of about 5 mm.

Said cylinders were dried and calcined in air at a temperature of 550° C., thereby obtaining $Cr_2O_3$ in crystalline form for about 80%, as revealed by X-ray analysis.

Fluorination reaction

Into an Inconel 600 tubular reactor having an inside diameter of 4 cm and a length of 80 cm, equipped with a porous bottom of sintered Inconel 600, heated by means of resistors, there were introduced 400 g of $Cr_2O_3$, prepared as described before, in the form of pellets having a diameter of 0.5 cm and a height of 1 cm.

The catalyst was dried for 2 hours at 400° C. in a $N_2$ flow.

About 1 mole/h of a mixture containing 96.5 moles-% of 134a, 1.6 moles-% of 1122, 1.5 moles-% of 133a and 0.4 moles-% of other organic chlorofluorinated compounds was fed at a temperature of 300° C.; furthermore, 0.1 moles/h of HF were fed.

During about 20 hours, the 1122 content in the flow leaving the reactor was less than 100 p.p.m., but no significant losses in main product 134a occurred. The disappeared 1122 resulted to be quantitatively converted into 133a.

After 20 hours, the catalyst was regenerated for being utilized again.

EXAMPLE 2

Into an Inconel 600 tubular reactor having an inside diameter of 9 mm and a length of 20 cm, equipped with a porous bottom of sintered Inconel 600, heated by means of resistors, there were introduced 3 g of $Cr_2O_3$ prepared as described hereinbefore, in the form of granules with size ranging from 140 to 325 mesh.

The catalyst was dried for 2 hours at 400° C. in a nitrogen flow.

At a temperature of 350° C., 190 mmoles/h of 134a, 3 mmoles/h of 1122 and 25 mmmoles/h of HF were fed.

During about 25 hours, the 1122 content in the outflow was by far below 100 p.p.m., without significant losses of main product 134a; all the disappeared 1122 had been converted into 133a.

After 25 hours the catalyst was regenerated for being utilized again.

EXAMPLE 3

Into an Inconel 600 tubular react-or having an inside diameter of 9 mm and a length of 20 cm, equipped with a porous bottom made of sintered Inconel 600, heated by means of resistors, there were introduced 2 g of crystalline $Cr_2O_3$, prepared as described hereinbefore, in the form of granules having diameter of about 1 mm.

The catalyst was dried for 2 hours at 400° C. in a nitrogen flow.

At a temperature of 300° C., 190 mmoles/h of 134a, 3 mmoles/h of 1122 and 25 mmoles/h of HF were fed.

During 35 hours, the 1122 content in the outflow was by far below 100 p.p.m., without significant losses of main product 134a; all the disappeared 1122 resulted to be converted into 133a.

After said period of time, the catalyst was regenerated so that it regained its initial activity.

EXAMPLE 4

A $Cr_2O_3$ catalyst in the form of small cylinders of about 5 mm diameter was prepared by the method described in example 1, except that calcination in air was effected at 700° C. instead of at 550° C.

Into a reactor similar to the one described in example 3, containing 2 g of chrome oxide so prepared, there were fed, at 320° C., 190 mmoles/h of 134a, 3 mmoles/h of 1122 and 25 mmoles/h of HF.

During 35 hours the 1122 content in the flow leaving the reactor was equal to about 20 p.p.m., without significant losses of 134a.

All the disappeared 1122 resulted to be converted into 133a.

After said period of time, the catalyst was regenerated, its initial activity being restored.

EXAMPLE 5

A carrier consisting of alumina fluorinated for 95% to $AlF_3$ prevailingly in the γ form, having a specific surface of about 27 $m^2/g$, was impregnated with 450 ml of an aqueous solution consisting of 492 g of $CrCl_3.3H_2O$ in 152 ml of $H_2O$. The impregnation was effected by adding such solution in three portions of approximately equal volume to the carier and by drying the catalyst after each addition for 4 hours at 120° C. at atmospheric pressure.

Lastly, the catalyst was charged into a tubular reactor and fluidized for 4 hours with an air flow at 400° C.

After such operation, the chrome oxide present on the carrier was for 65% in the crystalline form.

4 g of the catalyst so prepared were charged into a tubular reactor having an inside diameter of 6 mm.

At different reaction temperatures and with contact times ranging from 3 to 5 seconds, a gaseous stream composed of 134a (40 mmoles/h), $N_2$ (5 mmoles/h) and HF (15 mmoles/h) was fed to the reactor. The fed 134a contained, as an impurity, about 1 mole-% of 1122.

In each test the catalyst did not need to be regenerated for at least 10 hours of reagent feeding. The following table shows the 1122 concentrations, in p.p.m.—determined by gas chromatography at the reactor outlet —of the reaction products after absorption of the acidity, if any, in water.

| Reaction temperature (°C.) | 1122 in the reaction gases (p.p.m.) |
| --- | --- |
| 240 | 100 |
| 260 | <10 |
| 280 | <10 |
| 300 | <10 |
| 320 | <10 |
| 340 | <10 |
| 360 | <10 |
| 380 | 30 |
| 400 | 130 |

All the disappeared 1122 resulted to be converted into 133a, which can be recycled to the preparation of 134a.

We claim:

1. A process for purifying a mixture of 1,1,1-trifluoro-2-fluoroethane and a 1,1-difluoro-2-chloro-ethylene impurity, said process comprising reacting, at temperatures ranging from 200° to 450° C., said mixture with hydrofluoric acid in the presence of a chrome oxide catalyst in the non-carried form, wherein:

said chrome oxide catalyst being of a substantially crystalline structure such that at least 60% by weight of said chrome oxide catalyst is of a non-amorphous crystalline structure, and said chrome oxide catalyst having been prepared at a calcination temperature higher than 420° C. and UD to about 900° C.

2. The process of claim 1, in which the reaction temperature ranges from 250° to 380° C.

3. The process of claim 1, wherein the mixture comprising 1,1,1-trifluoro-2-fluoroethane and 1,1-difluoro-2-chloroethylene comes from the preparation of 1,1,1-tri-fluoro-2-floroethane via fluorination of trichloroethylene and/or of 1,1,1-trifluoro-2-chloroethane.

* * * * *

UNITED STATES PATENT AND TRADEMARK OFFICE
CERTIFICATE OF CORRECTION

PATENT NO.   : 5,475,168
DATED        : December 12, 1995
INVENTOR(S)  : Masiero, et. al.

It is certified that error appears in the above-indentified patent and that said Letters Patent is hereby corrected as shown below:

Column 5, line 7, delete ". and UD" and insert --and up--.

Signed and Sealed this

Seventh Day of May, 1996

Attest:

BRUCE LEHMAN

Attesting Officer  Commissioner of Patents and Trademarks